United States Patent
Sunier et al.

(10) Patent No.: US 9,224,658 B2
(45) Date of Patent: Dec. 29, 2015

(54) MEMBRANE-BASED SENSOR DEVICE WITH NON-DIELECTRIC ETCH-STOP LAYER AROUND SUBSTRATE RECESS

(71) Applicant: Sensirion AG, Stafa (CH)

(72) Inventors: Robert Sunier, Thalwil (CH); Cyrill Kuemin, Rapperswil (CH); Rene Hummel, Baar (CH)

(73) Assignee: Sensirion AG, Stafa (CH)

( * ) Notice: Subject to any disclaimer, the term of this patent is extended or adjusted under 35 U.S.C. 154(b) by 0 days.

(21) Appl. No.: 14/161,267

(22) Filed: Jan. 22, 2014

(65) Prior Publication Data

US 2014/0210036 A1 Jul. 31, 2014

(30) Foreign Application Priority Data

Jan. 31, 2013 (EP) .................................... 13405014

(51) Int. Cl.
| | |
|---|---|
| *G01N 27/04* | (2006.01) |
| *G01N 27/14* | (2006.01) |
| *H01L 21/84* | (2006.01) |
| *G01F 1/684* | (2006.01) |
| *G01N 27/12* | (2006.01) |

(52) U.S. Cl.
CPC .............. *H01L 21/84* (2013.01); *G01F 1/6845* (2013.01); *G01N 27/04* (2013.01); *G01N 27/128* (2013.01); *G01N 27/14* (2013.01)

(58) Field of Classification Search
CPC ................................................. G01N 27/4148
USPC ........................................... 257/467; 438/49
See application file for complete search history.

(56) References Cited

U.S. PATENT DOCUMENTS

| | | |
|---|---|---|
| 3,042,786 A | 7/1962 | Babcock et al. |
| 4,651,564 A | 3/1987 | Johnson et al. |
| 5,288,147 A | 2/1994 | Schaefer et al. |
| 5,596,219 A | 1/1997 | Hierold |
| 5,656,733 A | 8/1997 | Suchanec |

(Continued)

FOREIGN PATENT DOCUMENTS

| | | |
|---|---|---|
| EP | 0696725 | 2/1996 |
| EP | 1065475 | 1/2001 |

(Continued)

OTHER PUBLICATIONS

European Search Report No. 13405014.5 dated Jun. 21, 2013.

(Continued)

*Primary Examiner* — Marc Armand
*Assistant Examiner* — Younes Boulghassoul
(74) *Attorney, Agent, or Firm* — Cooper & Dunham LLP

(57) ABSTRACT

A sensing device has a semiconductor substrate with an opening and a membrane spanning the opening. A heater is arranged on the membrane. To reduce the thermal conductivity of the membrane, a recess is etched into the membrane from below.

20 Claims, 2 Drawing Sheets

(56) References Cited

U.S. PATENT DOCUMENTS

| | | | |
|---|---|---|---|
| 5,830,372 A | 11/1998 | Hierold | |
| 6,008,138 A * | 12/1999 | Laermer et al. | 438/725 |
| 6,565,765 B1 * | 5/2003 | Weber | 216/83 |
| 6,662,121 B1 | 12/2003 | Oda et al. | |
| 6,684,694 B2 | 2/2004 | Fujiwara et al. | |
| 6,871,538 B2 | 3/2005 | Fujuwara et al. | |
| 6,945,106 B2 | 9/2005 | Lotters | |
| 7,154,372 B2 * | 12/2006 | Vanha et al. | 338/42 |
| 7,490,511 B2 | 2/2009 | Mayer et al. | |
| 2002/0007674 A1 | 1/2002 | Leung | |
| 2003/0037590 A1 * | 2/2003 | Stark | 73/1.03 |
| 2003/0115952 A1 | 6/2003 | Mayer et al. | |
| 2003/0152128 A1 | 8/2003 | Verhaegen | |
| 2004/0075140 A1 * | 4/2004 | Baltes et al. | 257/347 |
| 2007/0231942 A1 * | 10/2007 | Vanha et al. | 438/50 |
| 2007/0241093 A1 | 10/2007 | von Waldkirch et al. | |
| 2009/0065472 A1 * | 3/2009 | Asai et al. | 216/27 |
| 2010/0314700 A1 * | 12/2010 | Park et al. | 257/414 |
| 2011/0138882 A1 * | 6/2011 | Moon et al. | 73/31.06 |
| 2014/0091422 A1 * | 4/2014 | Barth | 257/467 |
| 2014/0208828 A1 * | 7/2014 | Von Waldkirch | 73/25.05 |
| 2014/0208830 A1 * | 7/2014 | Buhler et al. | 73/31.06 |

FOREIGN PATENT DOCUMENTS

| | | |
|---|---|---|
| EP | 2348292 | 7/2011 |
| JP | 2000304584 | 11/2000 |
| JP | 2002048615 | 2/2002 |
| WO | 9519563 | 7/1995 |

OTHER PUBLICATIONS

P. Malcovati et al., "Combined Air Humidity and Flow CMOS Microsensor with On-Chip 15 Bit Sigma-Delta A/D Interface", Symposium on VLSI Circuits Digest of Technical Papers, XP000557797, Aug. 6, 1995, p. 45.

Jean Laconte et al., SOI CMOS Compatible Low-Power Microheater Optimization for the Fabrication of Smart Gas Sensors—IEEE Sensors Journal, vol. 4, No. 5, Oct. 2004, pp. 670-680.

* cited by examiner

MEMBRANE-BASED SENSOR DEVICE WITH NON-DIELECTRIC ETCH-STOP LAYER AROUND SUBSTRATE RECESS

TECHNICAL FIELD

The invention relates to a sensor device having a semiconductor substrate with an opening, a membrane extending over said opening and a heater located on the membrane. The invention also relates to a method for manufacturing such a sensor device.

BACKGROUND ART

Various sensor devices require a heater. One group of such devices is formed by flow sensors, where changes in the thermal distribution around the heater are used to measure a fluid flow. Such a device is e.g. disclosed in US 2007/0241093. Another group of such devices comprises gas sensors, where the heater is used to heat a sensing material, such as a metal oxide, to an operating temperature. A device using such a hot plate is e.g. disclosed in WO 95/19563.

This type of devices can be integrated onto a semiconductor substrate, in which case, the heater is advantageously arranged on a membrane over an opening in the semiconductor substrate, thereby reducing the thermal loss as compared to devices where the heater is arranged over the bulk of the substrate material. Arranging the heater on a membrane has a series of advantages, such as reducing power consumption, increasing sensitivity and reducing the time required for switching on the device.

DISCLOSURE OF THE INVENTION

According to a first aspect of the present invention, a sensor device comprises a semiconductor substrate (such as a silicon substrate) having a top and a bottom surface and an opening extending between the top and bottom surfaces. A batch of material layers, e.g. comprising structured dielectric and metallic or semiconducting layers, is arranged on the top surface of the substrate, e.g. in order to form conducting leads and other electrical and electronic components of the device. Some of the material layers extend over the opening of the semiconductor substrate, thereby forming a membrane. Further, a heater is arranged on the membrane.

In addition, the device comprises a recess extending from below into the batch of material layers at the location of the membrane, thereby reducing the thickness of the membrane and therefore thermal losses through the membrane.

A device of this type can be manufactured according to a second aspect of the present invention by providing a semiconductor substrate having a top and a bottom surface. The mentioned batch of material layers is applied to the top surface, and a heater is formed in the batch of material layers by suitable structuring techniques. Further, an opening is etched through the substrate, thereby forming a membrane formed by the material layers at the location of the heater. In addition, a recess is etched into the bottom side of the batch of material layers, namely by applying an etching agent through the opening in the substrate. In this manner, the thickness of the membrane is reduced.

This design is particularly advantageous when being combined with modern CMOS processes, where typically a very large batch of material layers is applied to the semiconductor substrate. This batch can have a thickness of 10 µm or more, even at locations where the metal layers are removed. By forming said recess in the membrane, the thickness of the membrane can be optimized.

Etching the recess from below has the further advantage that it does not affect the topography of the top surface of the batch of material layers, while forming the recess from above would lead to a non-flat surface of the membrane, which would render the formation of electrode structures and of other type of surface structures more difficult, in particular when using photolithography.

Typically, the batch of material layers comprises a plurality of structured dielectric layers and a plurality of structured metal layers, such as e.g. known from conventional CMOS devices. It can e.g. be manufactured by subsequent application of unstructured layers of suitable materials and structuring the same using photolithographic techniques.

Further, the batch of material layers advantageously comprises at least one non-dielectric etch-stop layer, which is structured to extend over the location of the opening to be formed in the substrate. This etch-stop layer is used as an etch-stop when forming the recess into the batch of material layers. Even though the etch-stop layer is not strictly necessary (timed etching could be used instead in order to etch the recess to a certain depth), it is advantageous since it allows to stop the etching-process at a well-defined location.

After etching the recess, at least part of the etch-stop layer may preferably be removed in order to further reduce the thermal conductivity of the membrane.

The sensor is advantageously a gas sensor or a flow sensor.

Other advantageous embodiments are listed in the dependent claims as well as in the description below.

BRIEF DESCRIPTION OF THE DRAWINGS

Embodiments of the present invention are described by reference to the annexed drawings, wherein.

MODES FOR CARRYING OUT THE INVENTION

Definitions

Terms indicating a vertical direction or arrangement, such as "top", "bottom", "above" or "below" relate to a frame of reference where the batch of material layers forming the membrane are arranged on top, i.e. above, the substrate. In other words, the substrate is arranged, by definition, below the material layers and the membrane is located on top of the opening extending through the substrate.

The term "lateral" is used to describe directions parallel to the top and bottom surfaces of the semiconductor substrate.

A "dielectric" material is a non-conductive, non-metallic material, in particular an oxide or nitride, such as $SiO_2$ or SiN.

A "non-dielectric" material is a metal or a metalloid.

An "SOI-structure" ("Silicon on Insulator") is a structure comprising a handle substrate of silicon, a silicon layer, and an insulator layer arranged between the handle substrate and the silicon layer.

Figure 1:
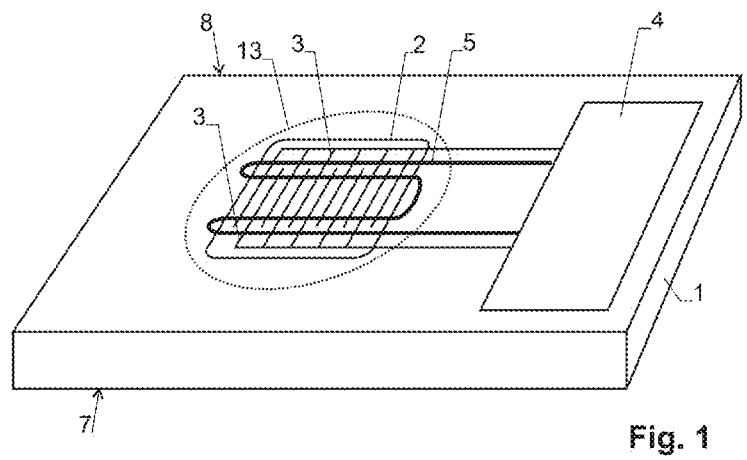
FIG. 1 shows a view of a sensor device.

The device:

FIG. 1 shows a gas sensor adapted to generate a signal indicative of the concentration of at least one gaseous analyte in a gaseous carrier, such as alcohol in air. It comprises a semiconductor substrate 1. A sensor material, whose electrical properties depend on the concentration of the analyte, is applied to substrate 1 in a patch 2. For example, patch 2 consists of a granular layer of SnO, whose electrical resistance depends on the presence and concentration of various compounds in the surrounding atmosphere. This type of device is e.g. described by WO 95/19563.

Patch 2 is in electrical contact with at least a pair of interdigital metal electrodes 3, which are connected to processing circuitry 4. Processing circuitry 4 is integrated on semiconductor substrate 1 and can e.g. comprise active components, such as transistors, at least one amplifier, at least one analog/digital converter, and/or interface circuitry, etc.

The sensor device further comprises a heater 5 positioned at the location of patch 2 in order to heat patch 2 to its operating temperature, which, for SnO, is e.g. typically at least 300° C.

Figure 2:
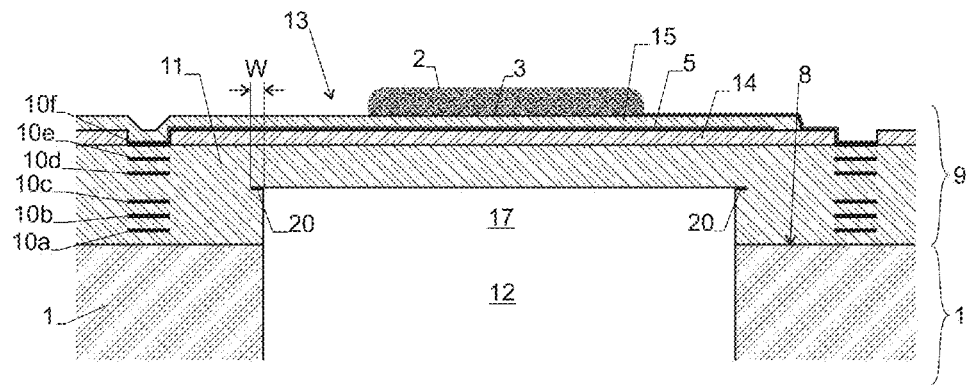
FIG. 2 shows a sectional view of the device.

FIG. 2 shows a sectional view of this type of device. As can be seen, semiconductor substrate 1 comprises a bottom surface 7 (cf. FIG. 1) and a top surface 8. A batch 9 of material layers is applied to top surface 8 and typically comprises a plurality of structured dielectric layers and a plurality of structured metal layers as used in standard CMOS processes.

Typically, the metal layers, which are generally designated by reference numbers 10a-10f, are of aluminum or copper, and they are structured to form leads and other electrical components. In FIG. 2, they are only shown schematically. The metal layers 10a-10f are separated by dielectric layers, typically $SiO_2$ layers, which are generally denoted by reference number 11.

Part of the layers of batch 9 extend over an opening 12 in semiconductor substrate 1 and form a membrane 13. Membrane 13 can have circular or rectangular cross section or any other suitable cross-section.

Advantageously, and in order to reduce the thermal conductance of membrane 13, none of the aluminum or copper metal layers 10a-10f extends into membrane 13.

Batch 9 further comprises a layer 14 of SiN under tensile stress, which extends at least over membrane 13 and is anchored laterally outside membrane 13. The tensile stress in layer 14 is at least sufficiently large to exceed the compressive stress in the rest membrane 13, which leads to a total tensile stress in the membrane. As described in U.S. Pat. No. 7,154,372, such a tensile layer can be used to prevent the membrane from buckling.

Heater 5 is formed by structuring a metal layer into at least one metal conductor, which is located on membrane 13. Advantageously, heater 5 is formed by a tungsten conductor. As seen in FIG. 1, the metal conductor can e.g. follow a meandering path. The layer of heater 5 is arranged on SiN layer 14.

A $SiO_2$ layer 15 is arranged on top of the layer of heater 5 and electrically insulates the same from a further metal layer forming the electrodes 3.

A protective dielectric layer can be applied to the top of the device (not shown).

As can be seen in FIG. 2, at the location of the membrane the device further comprises a recess 17 extending from below into the batch 9 of material layers. This recess has the purpose, as discussed above, to reduce the thickness of membrane 13.

Typically, batch 9 has a thickness of at least 5 μm, in particular between 6 and 15 μm. Recess 17 has a vertical depth of at least 1 μm, in particular of at least 3 μm.

The cross section, i.e. the lateral extension, of recess 17 is advantageously equal to the cross section of the upper end of opening 12, such that it spans the whole membrane, and the membrane therefore has a reduced thickness everywhere. Alternatively, the cross section area of recess 17 may be at least 80% of the cross section area of the upper end of opening 12.

Membrane 13 preferably has sufficiently large lateral extensions to provide a thermally insulated location for receiving patch 2. Advantageously, membrane 13 may cover an area of at least 0.1 $mm^2$, in particular at least 0.2 $mm^2$.

For reasons that will become apparent from the description of the manufacturing process below, the sensor device further comprises at least one etch-stop layer 20, or, rather, residual remains thereof, arranged in a ring around recess 17. Etch-stop layer 20 is of a non-dielectric material, in particular of aluminum or copper. The ring of etch-stop layer 20 has a lateral width W between 1-20 μm in order to be able to compensate for positioning errors in the etching process described below. The shape of the ring formed by edge-stop layer 20 depends on the shape of recess 17.

As can be seen, etch-stop layer 20 is advantageously positioned at a height between two of the metal layers 10a-10f, i.e. at an intermediate height of batch 9, namely at such a height that the distance between etch-stop layer 20 and the top of batch 9 corresponds to the desired thickness of the membrane.

Figure 3:
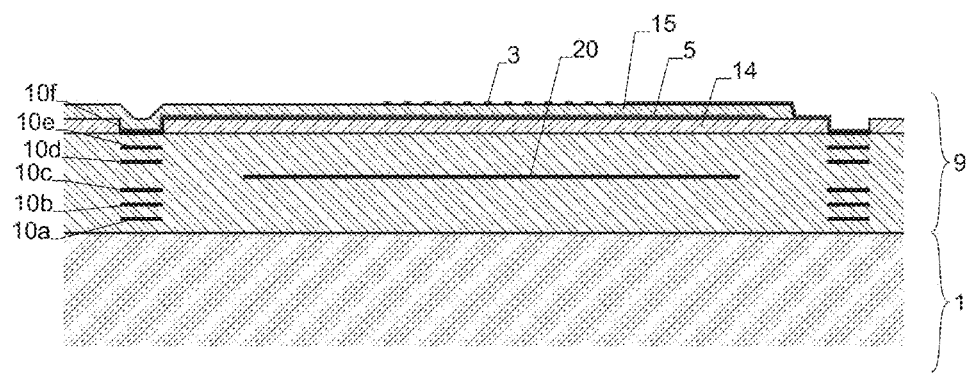
FIG. 3 shows a sectional view of the device after forming the batch of material layers.
Figure 4:
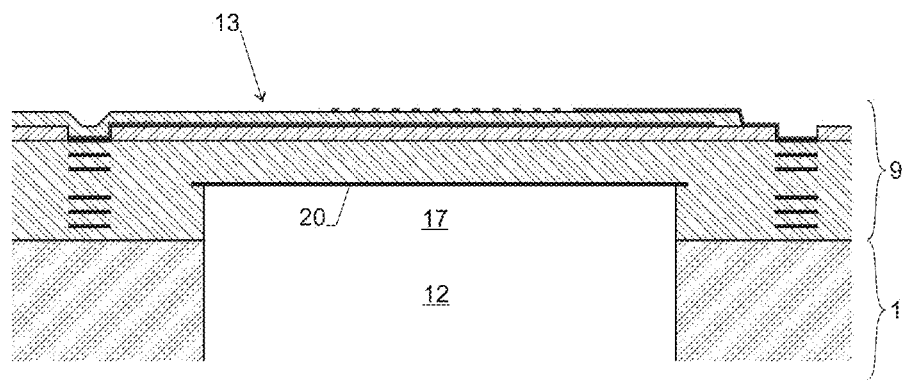
FIG. 4 shows a sectional view of the device after forming the recess.

Manufacturing Process:

FIGS. 3 and 4 show a method for manufacturing the sensor device.

In a first step, silicon substrate 1 is covered, at its top surface, with the dielectric layers 11 as well as with the metal layers 10a-10f in a series of steps as known in the art of semiconductor device manufacture. For example, a first $SiO_2$-layer is applied to top surface 8, then the first metal layer 10a is applied onto the first $SiO_2$-layer and structured using photolithography. Then, a second $SiO_2$-layer is applied, and the second metal layer 10b is applied thereto and structured, etc.

Between two of these steps, etch-stop layer 20 is applied and structured to extend over the area of future opening 12 and slightly beyond. For the reasons mentioned above, at least one first metal layer (in the embodiment of FIG. 3 the metal layers 10a-10c) is added to batch 9 of layers before etch-stop 20 layer is formed, and at least one second metal layer (10d-10f) is added to batch 9 of layers after etch-stop layer 20 is formed.

After applying the metal layers 10a-10f, etch-stop layer 20 and the dielectric layers 11, the layer for heater 5 is applied and structured, followed by the application of tensile layer 15 and the electrodes 3. This results in a device as shown in FIG. 3.

In a next step, opening 12 is etched out from the bottom side 7 of semiconductor substrate 1, e.g. using a plasma-process (such as deep reactive ion etching) or a wet process (such as anisotropic etching using KOH) after application of a photolithographic mask to bottom side 7. This step uses the bottom surface of the dielectric layers 11 as an etch-stop.

In a next step, recess 17 is etched. In this step, etch-stop layer 20 acts as an etch-stop. If recess 17 is to have the same lateral extension as opening 12, no masking is required in this step.

The resulting device is shown in FIG. 4.

In a next step, the accessible part of etch-stop layer 20 can optionally be removed by etching. A residual ring of the etch-stop layer 20 of width W surround recess 17, as described above, remains in the device.

Now, patch 2 of the sensing material can be applied to the top of membrane 13.

ALTERNATIVE EMBODIMENT

Figure 5:
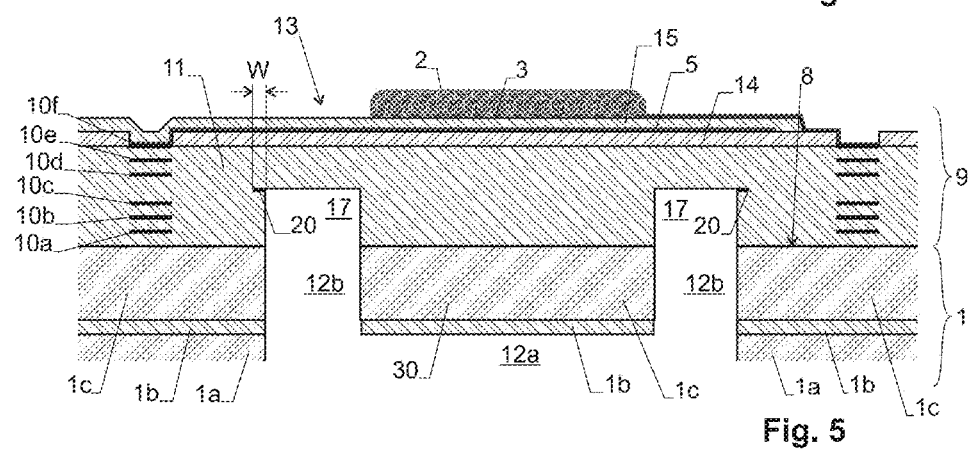
FIG. 5 shows a second embodiment of the device with a silicon plate arranged at the bottom of the membrane.

FIG. 5 shows an alternative design of the device with a silicon plate 30 arranged at the bottom of membrane 13. Silicon plate 30 is not connected to substrate 1, i.e. there is a gap between silicon plate 30 and substrate 1, which extends all around silicon plate 30 and is formed by opening 12 and recess 17. Recess 17 has annular shape.

The purpose of silicon plate 30 is to provide a uniform temperature distribution at the location of patch 2.

Plate 30 can have a thickness equal to substrate 1, in which case the device can be manufactured as described above with the sole difference that opening 12 has annular shape, thereby forming plate 30 from substrate 1.

Alternatively, and as shown in FIG. 5, plate 30 can have a thickness smaller than the thickness of substrate 1. To manufacture a sensor of this type, substrate 1 can be formed by an SOI structure. In other words, an SOI-wafer is used for manufacturing substrate 1. Such an SOI-waver comprises a handle substrate $1a$, an insulating layer $1b$ (in particular $SiO_2$) arranged on substrate $1a$, and a monocrystalline silicon layer $1c$ on top of insulating layer $1b$. Typically, the thickness of silicon layer $1c$ is much smaller than the thickness of handle substrate $1a$. This type of SOI-waver is known to the skilled person.

The batch of layers 9 is integrated on top of silicon layer $1c$.

For manufacturing opening 12 and recess 17, the device is again etched from its bottom side. In a first step, a first part $12a$ of opening 12 is formed, using insulating layer $1b$ as an etch stop. A mask is then applied on insulating layer $1b$ at the location of the future plate 30, and insulating layer $1b$ is removed outside this mask. Then, an annular second part $12b$ of opening 12 is formed by etching off silicon layer $1c$ where it is not masked, thereby forming plate 30 from silicon layer $1c$. Second part $12b$ forms the annular gap extending all around plate 30 between plate 30 and substrate 1. Finally, recess 17 is formed by etching from the side second part $12b$ of opening 12 as described above.

Flow Sensor:

As mentioned, the sensor device can also be a thermal flow sensor, e.g. of the type described in U.S. 2007/0241093, which has a heater arranged on the membrane. A fluid flowing over the membrane distorts the thermal field generated by the heater, which in turn can be detected by one or more suitable temperature sensors arranged on the membrane.

Figure 6:
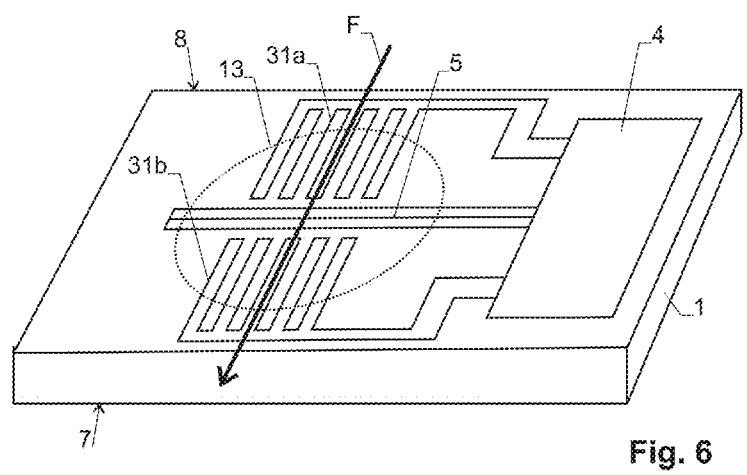
FIG. 6 shows a view of a flow sensor.
Note: The drawings are not to scale.

FIG. 6 shows such a flow sensor having an elongate heater 5 arranged on membrane 13, as well as at least one, in particular two temperature sensors $31a$, $31b$ on membrane 13. The two temperature sensors $31a$, $31b$ are arranged on both sides (upstream and downstream) of heater 5. The temperature sensors $31a$, $31b$ in the shown embodiment are thermopiles, as described in U.S. 2007/0241093. The device can be used to measure a flow F in a direction perpendicular to the elongate axis of heater 5.

Notes:

In the embodiment described in reference to FIGS. 1-5, the sensor device was a gas sensor having a metal oxide, in particular SnO, as sensing material. The device can, however, also be a gas sensor using another sensing material as known to the skilled person.

The sensor device may also be any other type of device where a heater is arranged on a thin membrane.

While there are shown and described presently preferred embodiments of the invention, it is to be distinctly understood that the invention is not limited thereto but may be otherwise variously embodied and practised within the scope of the following claims.

The invention claimed is:

1. A sensor device comprising
   a substrate having a top and a bottom surface and an opening extending between said top and bottom surfaces,
   a batch of material layers applied to said top surface, wherein at least some of said material layers extend over said opening for forming a membrane,
   a heater arranged on said membrane,
   wherein said sensor device comprises a recess extending from below into said batch of material layers at a location of said membrane,
   wherein said batch of material layers further comprises at least one non-dielectric etch-stop layer extending in a ring around said recess, and
   wherein said ring is at level with a to surface of the recess.

2. The sensor device of claim 1 wherein said recess has a depth of at least 1 µm.

3. The sensor device of claim 2, wherein said recess has a depth of at least 3 µm.

4. The sensor device of claim 1 wherein said recess has a cross section area of at least 80% of a cross section area of an upper end of said opening.

5. The sensor device of claim 4, wherein said recess has a cross section equal to the cross section of the upper end of said opening.

6. The sensor device of claim 1 wherein said batch of material layers comprises a plurality of structured dielectric layers and a plurality of structured metal layers.

7. The sensor device of claim 1, wherein said ring has a width between 1 and 20 µm.

8. The sensor device of claim 7, wherein said non-dielectric etch-stop layer is of aluminum or copper.

9. The sensor device of claim 1 wherein said membrane comprises at least one SiN-layer under tensile stress.

10. The sensor device of claim 1 further comprising
    at least one patch of a sensing material arranged on said membrane, and
    electrodes contacting said sensing material.

11. The sensor device of claim 10, wherein said at least one patch of a sensing material is a metal oxide.

12. The sensor device of claim 10, wherein said electrodes are metal electrodes.

13. The sensor device of claim 1 wherein said heater comprises at least one metal conductor.

14. The sensor device of claim 13, wherein said at least one metal conductor is a tungsten conductor.

15. The sensor device of claim 1 further comprising processing circuitry integrated on said substrate.

16. The sensor device of claim 15 wherein said processing circuitry comprises at least one amplifier, analog/digital-converter or interface circuitry.

17. The sensor device of claim 1 further comprising a silicon plate arranged at a bottom of said membrane, with a gap formed around said plate between said plate and said substrate.

18. The sensor device of claim 17, wherein said substrate is an SOI structure having a silicon handle layer, an insulating layer and a silicon layer, with said insulating layer arranged between said silicon handle layer and said silicon layer.

19. The sensor device of claim 1, wherein said sensor device is a gas sensor or a humidity sensor.

20. The sensor device of claim 1 wherein said sensor device is a flow sensor comprising at least one temperature sensor arranged on said membrane.

\* \* \* \* \*